United States Patent [19]

Ensminger

[11] Patent Number: 5,691,274
[45] Date of Patent: Nov. 25, 1997

[54] ANTIDOTING HERBICIDAL 3-ISOXAZOLIDINONE COMPOUNDS

[75] Inventor: Michael P. Ensminger, Petaluma, Calif.

[73] Assignee: Zeneca Limited, London, England

[21] Appl. No.: 638,253

[22] Filed: Apr. 26, 1996

Related U.S. Application Data

[63] Continuation of Ser. No. 278,485, Jul. 20, 1994, Pat. No. 5,527,761, and a continuation of Ser. No. 231,525, Apr. 22, 1994, Pat. No. 5,527,762, which is a continuation of Ser. No. 795,402, Nov. 26, 1991, Pat. No. 5,395,816, which is a continuation-in-part of Ser. No. 626,502, Dec. 12, 1990, abandoned.

[51] Int. Cl.$^6$ .................................. A01N 25/32
[52] U.S. Cl. .................................. 504/105
[58] Field of Search .................................. 504/105

[56] References Cited

U.S. PATENT DOCUMENTS

| | | | |
|---|---|---|---|
| 4,900,350 | 2/1990 | Ronchi | 504/105 |
| 5,201,933 | 4/1993 | Miller et al. | 504/104 |
| 5,225,570 | 7/1993 | Williams et al. | 504/107 |
| 5,256,626 | 10/1993 | Williams et al. | 504/107 |

Primary Examiner—Allen J. Robinson
Attorney, Agent, or Firm—Joel G. Ackerman

[57] ABSTRACT

This invention embodies compositions comprising herbicidally effective compounds corresponding to the formula

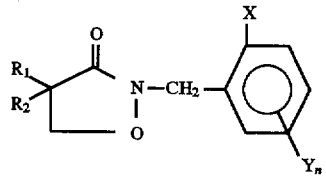

in which $R_1$ and $R_2$ are independently methyl or ethyl, X is H, methyl, chlorine, bromine, fluorine;

Y is chlorine, bromine, fluorine; and n is 0, 1 or 2 and a non-phytotoxic antidotally effective amount of an antidote therefor selected from the group of amides of haloalkanoic acids, including oxazolidines and thiazolidines, aromatic oxime derivatives, thiazole carboxylic acids and derivatives, substituted phenylpyrimidines, 2-(dichloroacetyl)-2-methyl-1,3-dioxolane and 2-(dichloromethyl)-2-thiazoline.

38 Claims, No Drawings

ANTIDOTING HERBICIDAL 3-ISOXAZOLIDINONE COMPOUNDS

This application is a continuation of application Ser. No. 08/278,485, filed Jul. 20, 1994, now U.S. Pat. No. 5,527,761 and of application Ser. No. 08/231,525, filed on Apr. 22, 1994, now U.S. Pat. No. 5,527,762 both of which are continuation applications of Ser. No. 07/795,402, filed Nov. 26, 1991 (now U.S. Pat. No. 5,395,816, issued Mar. 7, 1995), which is a continuation-in-part of application Ser. No. 07/626,502, filed Dec. 12, 1990 (now abandoned).

FIELD OF THE INVENTION

This invention pertains to herbicidal compositions and methods of use and more particularly to herbicidal compositions comprising 3-isoxazolidinone compounds and antidotes therefor which are useful as herbicides.

BACKGROUND OF THE INVENTION

Many herbicides injure crop plants at rates necessary to control weed growth. However, to be effective an herbicide must cause minimal damage, preferably no damage, to the beneficial crop while maximizing damage to weed species which infest the locus of the crop.

Herbicides have gained a high degree of commercial success because it has been shown that such compounds can increase crop yield and reduce harvesting costs. Some of these herbicides include types such as triazines, halogenated acetanilides, carbamates, thiolcarbamates, benzoic acid derivatives, urea derivatives and the like.

In some cases, a crop species may be susceptible to the effects of the herbicide. To preserve protection of crop species from herbicide injury along with the concomitant herbicidal effectiveness of weed species, use of chemical compounds called antidotes or safeners have been employed. See, for example, U.S. Pat. Nos. 4,021,224 and 4,230,874.

Although the effects of antidotes against herbicide injury can be established under field and greenhouse conditions the physiological and biochemical mechanisms of action have not been established for all compounds. Nevertheless, the use of antidote compounds with herbicides is a widely accepted agronomic practice. These compounds are used on crops including agronomic and vegetable species.

The isoxazolidinone compounds have been found to be very effective herbicides with broad general herbicidal activity against a wide variety of plant species. Many active 3-isoxazolidinone herbicidal compounds are disclosed in U.S. Pat. No. 4,405,357 which is incorporated herein in its entirety by reference. The method of controlling vegetation with the compounds comprises applying an herbicidally effective amount of the isoxazolidinone, usually with an inert carrier, to the area where herbicidal control is desired.

The isoxazolidinone compounds have been found in some instances to adversely affect or interfere with the culture of a variety of crops. In particular, gramineous crops such as corn are sensitive to the application of effective weed controlling rates. Therefore, the effective use of these herbicides for controlling weeds in the presence of such crops is further enhanced by, or may require in many instances, the addition of an antidotally effective amount of a compound, which is antidotally effective with the isoxazolidinone herbicide.

It is the objective of this invention to increase the spectrum of crop plants in which an active herbicidal 3-isoxazolidinone compound may be used without injury to the crop and without decreasing the herbicidal efficacy against weeds.

SUMMARY OF THE INVENTION

This invention comprises novel herbicidal compositions which provide excellent protection for a variety of crops from adverse herbicidal injury which composition comprises an herbicidally effective amount of a 3-isoxazolidinone and a substantially non-phytotoxic, antidotally-effective amount of an herbicide antidote, selected from the group consisting of amides of haloalkonoic acids, aromatic oxime derivatives, thiazole carboxylic acids and derivatives and substituted phenylpyrimidines.

In a preferred embodiment the composition also includes a second or co-herbicide preferably a thiolcarbamate, in particular S-ethyl dipropyl thiolcarbamate.

The invention also comprises a method for controlling undesirable vegetation in the presence of a crop, particularly corn, by applying to the locus of the crop or undesired vegetation an herbicidal composition as described hereinabove.

DETAILED DESCRIPTION OF THE INVENTION

Herbicidal 3-isoxazolidinones are described in U.S. Pat. No. 4,405,357 issued Sep. 30, 1983, along with methods for their preparation.

An especially preferred compound is 2-[2-chlorophenyl] methyl-4,4 dimethyl-3-isoxazolidinone, example 16 of the above-identified Patent. This compound, COMMAND®, is a commercially available herbicide known by the generic name clomazone. Clomazone is phytotoxic to certain crops when applied at rates effective to control undesired vegetation.

One method for production of COMMAND® is disclosed in U.S. Pat. No. 4,405,357. Such preparation includes adding to a stirred solution of 6.3 grams (0.023 mole) of 3-chloro-N-(2-chlorophenyl)methyl-N-hydroxy-2,2-dimethylpropanamide in 45 ml of methanol dropwise a solution of 1.5 grams (0.023 mole) KOH (85% pure) in 25 ml methanol. The addition required 15 minutes and the temperature rose from 24° to 32° C. Upon completion of addition the reaction mixture was stirred for 18 hours at ambient temperature. By-product KCl was removed by filtering the mixture. The filtrate was poured into 500 ml of ice-water. The mixture was extracted with two portions of 250 ml each of methylene chloride. The combined extracts were dried with $MgSO_4$ and filtered. Under reduced pressure the filtrate was concentrated to give 5.2 grams of 2-(2-chlorophenyl)methyl-4,4-dimethyl-3-isoxazolidinone as an oil.

Other substituted 4,4-dimethyl-3-isoxazolidinone herbicidal compounds may be prepared in the manner described hereinabove, by varying the reactant compound and amount and the grams of KOH in each case. For example, 2-(2-bromophenyl)methyl-4,4-dimethyl-3-isoxazolidinone can be prepared by using N-(2-bromophenyl)methyl-3-chloro-N-hydroxy-2,2-dimethyl propanamide and 0.75 g of 85% pure KOH in 40 ml of methanol.

The active 3-isoxazolidinones of this invention will generally be applied in diluted form for preemergence or preplant incorporation for effective control of many broadleaved and grassy weed species. The active compounds of this invention may be applied from a tank mix with other herbicides.

A wide range of chemical substances have been found to be effective as herbicide antidotes, and the preferred compositions of this invention include any one or more of such antidotes with the active isoxazolidinone herbicides. The variety of crops on which the above described herbicides are useful can be significantly broadened by the use of an antidote to protect one of more crops from injury therefrom and render the composition more selective against weeds. Some of the more important types of antidotes are amides of haloalkanoic acids, aromatic oxime derivatives, thiazole carboxylic acids and derivatives, naphthopyranone derivatives and substituted phenylpyrimidines.

Amides of haloalkanoic acids have the generalized formula

in which R is a mono- or poly-haloalkyl group. The halogens may be variously chloro, bromo or iodo; chloro is the preferred halogen, and the preferred group for R in these compounds in general is dichloromethyl, $Cl_2CH-$, i.e.,.the compounds are amides of dichloroacetic acid. In such compounds the nitrogen is further substituted by at least one other functional group or forms a portion of a heterocyclic ring, as will be described below.

Antidotes of this type are described in a number of publications such as U.S. Pat. Nos. 4,021,224; 4,256,481; 4,294,764; 4,900,350; European Patent Application, Publication No. 104,495, International Patent Application WO 81/406, and British Patent 1,521,540. U.S. Pat. No. 4,021,224 contains a broad disclosure of such types of compounds and indicates a great many possibilities for mono- or di-substitution on the nitrogen atom.

One type of antidote disclosed in U.S. Pat. No. 4,021,224 is N,N-diallyl dichloroacetamide,

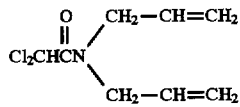

which is generally known commercially as R-25788 or dichlormid.

Another class of haloalkanoic acid amides is that in which the nitrogen atom in the foregoing formula is contained in a heterocyclic ring, for instance an oxazolidine or thiazolidine ring. Preferably R is dichloromethyl, and the preferred compounds have the general formula

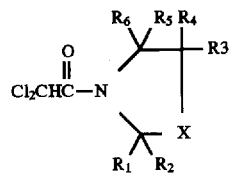

In this formula, X is oxygen or sulfur, and R1–R6 are variously independently hydrogen, lower alkyl, alkoxyalkyl, alkylthioalkyl, dialkylaminomethyl, methylcarboxyalkyl, lower alkysulfonylmethyl or phenyl, or $R_1$ and $R_2$ taken together form an alkylene group, preferably a butylene, pentylene or hexylene group, optionally substituted by one or two methyl groups. Compounds of these types are disclosed, for instance, in U.S. Pat. Nos. 4,021,224, 4,256, 481, 4,900,350, European Patent Application No. 104,495 and International Patent Application WO 81/406.

A preferred group of these compounds has the above formula in which X is oxygen or sulfur; $R_1$ is hydrogen, $C_1$–$C_6$alkyl or methylcarboxy ($C_1$–$C_3$) alkyl; $R_2$ is hydrogen or $C_1$–$C_6$alkyl; or $R_1$ and $R_2$ taken together form a butylene, pentylene or hexylene group optionally substituted by one or two methyl groups; $R_3$ is hydrogen, $C_1$–$C_6$ alkyl, $C_2$–$C_4$ alkoxyalkyl, phenyl or di-($C_1$–$C_4$ alkyl)aminomethyl (in which the alkyl groups may be the same or different; $R_4$ is hydrogen or $C_1$–$C_6$ alkyl; and $R_5$ and $R_6$ are independently hydrogen or $C_1$–$C_6$ alkyl (preferably hydrogen).

Representative compounds of this type include (where not specified, the substituent is hydrogen):

Oxazolidines (X=oxygen)

2,2-dimethyl-N-dichloroacetyl oxazolidine ($R_1$ and $R_2$=methyl);

2,2-5 trimethyl-N-dichloroacetyl oxazolidine ($R_1$, $R_2$ and $R_3$=methyl);

2,2-dimethyl-5-n-propyl-N-dichloroacetyl oxazolidine ($R_1$, $R_2$=methyl, $R_3$=n-propyl);

2,2-spirocyclohexyl-N-propyl-N-dichloroacetyl oxazolidine ($R_1$ plus $R_2$ taken together=pentamethylene);

2,2-dimethyl-N-dichloroacetyl-5-ethyl oxazolidine ($R_1$, $R_2$=methyl, $R_3$=ethyl);

2,2-dimethyl-5-phenyl-N-dichloroacetyl oxazolidine ($R_1$, $R_2$=methyl, $R_3$=phenyl);

2,2-dimethyl-5-(diisobutylaminomethylene)-N-dichloroacetyl oxazolidine ($R_1$, $R_2$=methyl; $R_3$=(N,N-diisobutylamino) methylene;

Thiazolidine (X=sulfur)

2-methyl, 2-methylcarboxymethyl-N-dichloroacetyl thiazolidine ($R_1$=methyl, $R_2$=$CH_2COOCH_3$);

2,2 dimethyl-N-dichloroacetyl thiazolidine ($R_1$ and $R_2$=methyl)

Other compounds in which $R_1$ and $R_2$ taken together are alkylene are disclosed for instance in British Patents 1,512, 540 and 2,023,582 and Hungarian Patent 181,621.

A third type of haloalkanoic acid amide is disclosed generally in U.S. Pat. No. 4,294,764 and has the general formula

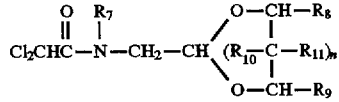

in which $R_7$ may be one of a number of alkyl, alkenyl or alkynyl moieties; $R_8$, $R_9$, $R_{10}$ and $R_{11}$ are independently hydrogen or methyl; and n is 0 or 1. A representative compound of this type is the compound N-(1,3-dioxolan-2-yl-methyl)-N-(2-propenyl)-2,2-dichloroacetamide, which has the formula

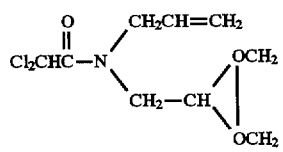

This corresponds to the previous formula in which $R_7$ is 2-propenyl, $R_8$ and $R_9$ are both hydrogen and n is 0.

A fourth type of haloalkanoic acid amide is disclosed in U.S. Pat. Nos. 4,601,745 and 4,618,361, and has the general formula

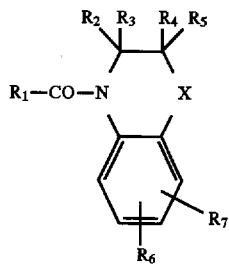

in which, among others, $R_1$ is $C_1-C_6$ haloalkyl, $R_2-R_5$ are independently hydrogen or $C_1-C_4$ alkyl, $R_6$ and $R_7$ are hydrogen, halogen, and a number of other substituents, and X is oxygen, sulfur, —SO— or —SO$_2$. Preferably $R_1$ is dichloromethyl and X is oxygen. A preferred member of this group is 4-(dichloroacetyl)-3,4-benzoxazine ($R_1$= dichloromethyl; $R_2$=methyl; $R_3-R_7$=hydrogen; X=oxygen), also known as CGA-154281.

Substituted phenylpyrimidines are disclosed in U.S. Pat. No. 4,493,726 and have the general formula

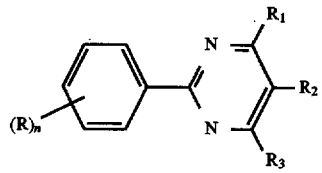

in which R is hydrogen or a number of substituents; n is an integer from 1 to 5; $R_1$ and $R_3$ are independently halogen or a number of substituents and $R_2$ is hydrogen, halogen, $C_1-C_6$ alkyl, $C_1-C_6$ haloalkyl or phenyl. One member of this group is 4,6-dichloro,2-phenylpyrimidine (R=hydrogen, $R_1$ and $R_3$=chlorine; $R_2$=hydrogen), also known as fenchorim or CGA-123407.

Oxime derivatives which are suitable for use as antidotes with herbicides are disclosed, for instance, in U.S. Pat. Nos. 4,070,389 and 4,269,775 and have the general formula

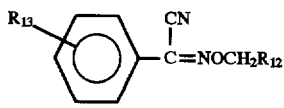

in which $R_{13}$ is optionally hydrogen, methyl, methoxy, chlorine, cyano or trifluoromethyl, and in which $R_{12}$ is cyano or a number of other moieties as indicated in U.S. Pat. No. 4,269,775. Representative compounds of this type are those in which $R_{12}$ is cyano and in which $R_{13}$ is 1,3 dioxolan-2-yl. The latter compound has the chemical name O-[2-(1,3-dioxolanyl)methyl]-alpha-cyano-benzaldoxime.

Thiazole carboxylic acids and derivatives suitable for use as antidotes are disclosed generally in U.S. Pat. No. 4,199,506 and have the general formula

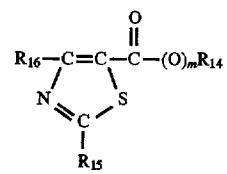

in which $R_{16}$ is alkyl, haloalkyl or trialkoxymethyl; $R_{14}$ is variously hydrogen, agriculturally acceptable cations or various hydrocarbamyl or substituted hydrocarbamyl moieties; m is 0 or 1 and $R_{15}$ is chloro, bromo, iodo, lower alkoxy or substituted or unsubstituted phenoxy. A representative member of this class is the compound benzyl-2-chloro-4-trifluoromethyl-5-thiazole carboxylate ($R_{16}$= trifluoromethyl; $R_{14}$=benzyl, $R_{15}$=chloro; m=1).

Two other antidotes which may be used with the active isoxazolidinone herbicide in compositions according to this invention are:

2-(dichloromethyl)-2-methyl-1,3-dioxolane:

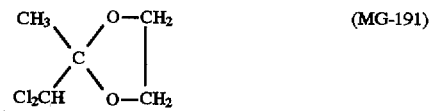

(MG-191)

(Disclosed in European Patent Application #198,879) and 2-(dichloromethyl)-2-thiazoline:

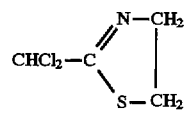

The amount of a given antidote to be utilized in combination with the herbicide composition of this invention and the manner of its utilization and resulting efficacy can vary according to various parameters such as the particular antidote to be employed, the crop which is to be protected, the amount or rate of herbicide to be applied, and the soil and climatic conditions of the agricultural environment in which the mixture is to be applied. The selection of a specific antidote for use in the herbicide composition, the manner in which it is to be applied (e.g., tank mix, infurrow application, seed treatment, etc.), the determination of activity which is non-phytotoxic but antidotally effective, and the amount necessary to provide this result, can be readily performed utilizing the test procedures in the cited patents such as U.S. Pat. No. 4,021,224, in accordance with common practice in the art.

The antidote is applied in conjunction with the herbicide in a non-phytotoxic antidotally effective amount. "Non-phytotoxic" is defined as an amount of the antidote which causes at most minor or no injury to the desired crop species. "Antidotally effective" is defined as an antidote used in an amount which is effective as an antidote with the herbicide to decrease the extent of injury caused by the herbicide to the desired crop species.

"Herbicidally effective" is defined as the amount of herbicide required to effect a meaningful injury or destruction of a significant portion of affected undesired weeds or plants.

Another embodiment of this invention includes thiolcarbamate co-herbicides in the composition comprising 3-isoxazolidinone compounds and antidotes thereof. Co-herbicidal compounds of preference include the following:

S-ethyl dipropyl thiolcarbamate

S-ethyl diisobutyl thiolcarbamate

S-propyl dipropyl thiolcarbamate

S-2,3,3-trichloroallyl diisopropyl thiolcarbamate

S-ethyl N-cyclohexyl N-ethylthiolcarbamate

S-ethyl bis-(2-methylpropyl) carbamothioate

All of the above specifically-named herbicides are known in the art, and they are described in U.S. Pat. Nos. 2,913,327 and 3,330,643.

Still other classes of herbicidal compounds contemplated for combination with this invention include acetamide herbicides such as alachlor, butachlor, acetochlor and metolachlor; S-triazine herbicides such as metribuzin; p-toluidine herbicides such as trifluralin; sulfonylurea herbicides such as nicosulfuron and primisulfuron; benzoic acid derivatives such as dicamba and the like.

In some cases it may be advantageous to also include in the composition a substance which can provide extension in time of the activity of thiolcarbamate herbicides, in an amount effective to extend this activity. Such substances are generally referred to as "thiocarbamate herbicide extenders." A number of substances have been found which possess these properties. Examples of such substances are certain types of organophosphorus compounds, carbamates and amines, which are disclosed respectively in European Patent Applications Publication Nos. 10,178, 38,945, and 78,146 and a number of carbamates, thiocarbamates and dithiocarbamates as disclosed in Canadian Patent No. 1,262,059. These patent applications disclose tests for determining whether a substance has such extending activity, and determining what amount of substance is required in a given case to provide this activity. As with the antidotes, such thiocarbamate herbicide extenders may be physically incorporated into the herbicidal composition or applied separately to the same ultimate locus. Preferred extenders in such compositions are the compound O,O-diethyl-O-phenyl phosphorothioate, disclosed for such use in European Patent Application, Publication No. 10,178 and N,N-bis(3-chloroallyl) S-ethyl thiocarbamate, disclosed in the Canadian Patent No. 1,262,059.

The herbicidal compositions according to this invention contain the 3-isoxazolidinone and antidotes in a weight ratio, respectively, of from about 0.1:1.0 to about 30:1 (exclusive of auxiliary ingredients). Another preferred weight ratio is from about 1:1 to about 20:1. An even more preferred weight ratio from about 2:1 to about 15:1.

Biological Evaluation

The following examples are provided for illustrative purposes only and are not intended as necessarily representative of the overall testing performed and are not intended to limit the invention in any way. As one skilled in the art is aware, in herbicidal testing, a significant number of factors that are not readily controllable can affect the results of individual tests. Results may vary depending on environmental factors, depth of planting, the application rate of the herbicide and antidote, the ratio of components in an herbicidal composition and the nature of plants being tested. Additionally results may vary from crop to crop and within varieties.

The following antidotes were employed in Example I and in Tables I and II:

1=N,N-diallyl dichloroacetamide

2=2,2,5-trimethyl-N-dichloroacetyl oxazolidine

3=2,2 dimethyl-N-dichloroacetyl thiazolidine

The following hybrids of corn were employed in Example I and in Tables I, II:

A=CN 8415

B=CN 7751

C=CN 6595

D=CN 7780

E=CN 3901

EXAMPLE I

The herbicide COMMAND® and antidotes as described hereinabove were applied preemergence onto soil in aluminum flats (10×21×6 cm deep) from a tank mix solution with a carrier volume of 25 gal/A. Seeds were planted 2 cm deep, in a sandy loam soil with pH 6.7, 0.8% organic matter and 8.9% clay. The soil was fortified with 17—17—17 fertilizer and the fungicide Captam 80W. Five hybrids of corn were utilized as summarized hereinabove. Additionally, green foxtail (Setaria viridis) was planted.

After treatment, all flats were placed into a greenhouse. Greenhouses were maintained at about 25° C. and 20° C., day and night temperature, respectively. All flats were watered to field capacity. Visual ratings of weed control and crop injury were recorded 9 days after treatment (Table I) and 27 days after treatment (Table II) corresponding to early rating data and late rating data. Ratings are stated as percentage of weed control of each weed species as compared with an untreated control. The control ratings range from 0 to 100%, where 0 represents no effect on growth and 100 represents complete kill. Additionally, ratings are stated as percent tolerance for individual corn varieties, where 0 represents no effect on a given parameter and 100 represents complete effect on a given parameter.

Good protection from bleaching and stunting resulted in corn with antidote compounds at the early rating (Table I) with lower rates of COMMAND®.

Late ratings (Table II) indicate that corn itself would outgrow the lower level of injury observed at lower COMMAND® application rates, however, the lower rate of injury that appeared in the early ratings indicate that the antidotes could be used to eliminate the bleaching symptoms that appear due to carryover, or eliminate unacceptable early injury to corn.

TABLE I

| | | | Corn Variety Tolerance | | | | | | | | | | |
|---|---|---|---|---|---|---|---|---|---|---|---|---|---|
| | | | A | | B | | C | | D | | E | | AVG |
| | Rate | Green | | | | | | | | | | | | |
| Herbicide & Antidote | (lb/A) | Foxtail | 1 | 2 | 1 | 2 | 1 | 2 | 1 | 2 | 1 | 2 | 1 | 2 |
| COMMAND ® | 0.03125 + 0 | 65 | 65 | 30 | 40 | 0 | 30 | 10 | 5 | 5 | 0 | 20 | 28 | 13 |
| COMMAND ® + 1 | 0.03125 + 0.25 | 65 | 20 | 15 | 5 | 5 | 0 | 0 | 3 | 0 | 0 | 0 | 6 | 4 |

MEAN PERCENT CORN TOLERANCE AND WEED CONTROL
NINE DAYS AFTER TREATMENT

TABLE I-continued

MEAN PERCENT CORN TOLERANCE AND WEED CONTROL NINE DAYS AFTER TREATMENT

| Herbicide & Antidote | Rate (lb/A) | Green Foxtail | A | | B | | C | | D | | E | | AVG | |
|---|---|---|---|---|---|---|---|---|---|---|---|---|---|---|
| | | | 1 | 2 | 1 | 2 | 1 | 2 | 1 | 2 | 1 | 2 | 1 | 2 |
| | 0.03125 + 0.5 | 35 | 5 | 0 | 0 | 5 | 0 | 0 | 0 | 10 | 0 | 10 | 1 | 5 |
| | 0.03125 + 1.0 | 55 | 5 | 5 | 0 | 5 | 0 | 0 | 5 | 0 | 0 | 5 | 2 | 3 |
| COMMAND ® + 2 | 0.03125 + 0.125 | 70 | 10 | 5 | 5 | 5 | 3 | 0 | 15 | 10 | 0 | 10 | 7 | 6 |
| | 0.03125 + 0.25 | 35 | 0 | 0 | 0 | 0 | 0 | 0 | 0 | 0 | 0 | 5 | 0 | 1 |
| | 0.03125 + 0.50 | 65 | 0 | 10 | 0 | 10 | 0 | 10 | 10 | 5 | 0 | 10 | 2 | 9 |
| COMMAND ® + 3 | 0.03125 + 0.125 | 40 | 3 | 5 | 15 | 10 | 3 | 5 | 3 | 5 | 0 | 5 | 5 | 6 |
| | 0.03125 + 0.25 | 40 | 0 | 0 | 0 | 0 | 0 | 0 | 0 | 0 | 0 | 5 | 0 | 1 |
| COMMAND ® | 0.03125 + 0.50 | 45 | 0 | 0 | 0 | 5 | 0 | 5 | 0 | 10 | 0 | 10 | 0 | 6 |
| Control | 0 + 0 | 0 | 0 | 5 | 0 | 5 | 0 | 5 | 0 | 5 | 0 | 10 | 0 | 6 |
| COMMAND ® | 0.0625 + 0 | 70 | 60 | 5 | 60 | 0 | 40 | 5 | 40 | 10 | 0 | 5 | 40 | 5 |
| COMMAND ® + 1 | 0.0625 + 0.25 | 75 | 25 | 15 | 20 | 10 | 20 | 10 | 5 | 0 | 0 | 0 | 14 | 7 |
| | 0.0625 + 0.5 | 40 | 40 | 10 | 25 | 10 | 10 | 5 | 0 | 5 | 0 | 0 | 15 | 6 |
| | 0.0625 + 1.0 | 75 | 35 | 10 | 35 | 10 | 40 | 0 | 35 | 10 | 5 | 5 | 30 | 7 |
| COMMAND ® + 2 | 0.0625 + 0.125 | 85 | 35 | 5 | 30 | 0 | 15 | 5 | 20 | 10 | 0 | 10 | 20 | 6 |
| | 0.0625 + 0.25 | 60 | 10 | 5 | 5 | 5 | 3 | 10 | 3 | 5 | 0 | 5 | 4 | 6 |
| | 0.0625 + 0.5 | 95 | 30 | 10 | 30 | 5 | 10 | 5 | 10 | 5 | 0 | 10 | 16 | 7 |
| COMMAND ® + 3 | 0.0625 + 0.125 | 95 | 15 | 5 | 15 | 10 | 5 | 15 | 25 | 5 | 5 | 15 | 13 | 10 |
| | 0.0625 + 0.25 | 75 | 10 | 5 | 0 | 5 | 0 | 0 | 3 | 0 | 0 | 5 | 3 | 3 |
| | 0.0625 + 0.50 | 85 | 10 | 5 | 0 | 10 | 3 | 10 | 5 | 5 | 0 | 10 | 4 | 8 |
| Control | 0 + 0 | 0 | 0 | 0 | 0 | 0 | 0 | 10 | 0 | 10 | 0 | 5 | 0 | 5 |
| COMMAND ® | 0.125 + 0 | 95 | 85 | 10 | 75 | 35 | 70 | 10 | 70 | 5 | 20 | 0 | 64 | 12 |
| COMMAND ® + 1 | 0.125 + 0.25 | 95 | 75 | 15 | 65 | 15 | 60 | 10 | 75 | 10 | 5 | 10 | 56 | 12 |
| | 0.125 + 0.5 | 95 | 40 | 15 | 35 | 5 | 25 | 10 | 40 | 0 | 0 | 5 | 28 | 7 |
| | 0.125 + 1.0 | 95 | 85 | 30 | 60 | 15 | 50 | 0 | 70 | 0 | 0 | 10 | 53 | 11 |
| COMMAND ® + 2 | 0.125 + 0.125 | 95 | 60 | 15 | 60 | 10 | 40 | 5 | 40 | 10 | 5 | 10 | 41 | 10 |
| | 0.125 + 0.25 | 95 | 40 | 0 | 35 | 0 | 30 | 5 | 40 | 15 | 3 | 5 | 30 | 5 |
| | 0.125 + 0.50 | 100 | 60 | 15 | 50 | 10 | 40 | 10 | 70 | 5 | 35 | 5 | 51 | 9 |
| COMMAND ® + 3 | 0.125 + 0.125 | 98 | 50 | 5 | 70 | 0 | 60 | 0 | 75 | 0 | 5 | 0 | 52 | 1 |
| | 0.125 + 0.25 | 95 | 35 | 20 | 30 | 15 | 25 | 5 | 15 | 0 | 0 | 5 | 21 | 9 |
| | 0.125 + 0.50 | 95 | 40 | 10 | 40 | 10 | 15 | 10 | 20 | 10 | 0 | 10 | 23 | 10 |
| Control | 0 + 0 | 0 | 0 | 15 | 0 | 0 | 0 | 5 | 0 | 5 | 0 | 0 | 0 | 5 |
| COMMAND ® | 0.25 + 0 | 95 | 75 | 10 | 75 | 10 | 65 | 5 | 75 | 5 | 70 | 5 | 72 | 7 |
| COMMAND ® + 1 | 0.25 + 0.25 | 100 | 90 | 10 | 80 | 5 | 75 | 5 | 80 | 10 | 60 | 10 | 77 | 8 |
| | 0.25 + 0.5 | 100 | 75 | 10 | 75 | 15 | 65 | 10 | 75 | 15 | 35 | 10 | 65 | 12 |
| | 0.25 + 1.0 | 100 | 80 | 10 | 80 | 15 | 70 | 10 | 75 | 10 | 50 | 5 | 71 | 10 |
| COMMAND ® + 2 | 0.25 + 0.125 | 100 | 80 | 10 | 80 | 10 | 75 | 10 | 85 | 15 | 40 | 0 | 72 | 9 |
| | 0.25 + 0.25 | 100 | 70 | 10 | 70 | 10 | 75 | 10 | 75 | 10 | 3 | 10 | 59 | 10 |
| | 0.25 + 0.50 | 100 | 75 | 15 | 75 | 15 | 60 | 15 | 75 | 15 | 40 | 15 | 65 | 15 |
| COMMAND ® + 3 | 0.25 + 0.125 | 100 | 75 | 15 | 75 | 10 | 65 | 10 | 85 | 15 | 65 | 0 | 73 | 10 |
| | 0.25 + 0.25 | 95 | 50 | 10 | 25 | 5 | 25 | 5 | 50 | 5 | 5 | 5 | 31 | 6 |
| | 0.25 + 0.50 | 100 | 60 | 15 | 40 | 15 | 40 | 20 | 50 | 5 | 15 | 5 | 41 | 12 |
| Control | 0 + 0 | 0 | 0 | 0 | 0 | 10 | 0 | 5 | 0 | 5 | 0 | 5 | 0 | 5 |

COMMAND ®, 2-(2-chlorophenyl)methyl-4,4-dimethyl-3-isoxazolidinone
1 = Pigment loss (incidence of bleaching and chlorosis)
2 = Stunting

TABLE II

MEAN PERCENT CORN TOLERANCE AND WEED CONTROL 27 DAYS AFTER TREATMENT

| Herbicide & Antidote | Rate (lb/A) | Green Foxtail | A | | B | | C | | D | | E | | AVG | |
|---|---|---|---|---|---|---|---|---|---|---|---|---|---|---|
| | | | 1 | 2 | 1 | 2 | 1 | 2 | 1 | 2 | 1 | 2 | 1 | 2 |
| COMMAND ® | 0.03125 + 0 | 25 | 5 | 0 | 0 | 0 | 0 | 0 | 0 | 0 | 0 | 0 | 1 | 0 |
| COMMAND ® + 1 | 0.03125 + 0.25 | 25 | 0 | 0 | 0 | 0 | 0 | 0 | 0 | 0 | 0 | 0 | 0 | 0 |
| | 0.03125 + 0.50 | 0 | 0 | 0 | 0 | 0 | 0 | 0 | 0 | 0 | 0 | 0 | 0 | 0 |
| | 0.03125 + 01.0 | 40 | 0 | 0 | 0 | 0 | 0 | 0 | 0 | 0 | 0 | 0 | 0 | 0 |

TABLE II-continued

MEAN PERCENT CORN TOLERANCE AND WEED CONTROL
27 DAYS AFTER TREATMENT

| Herbicide & Antidote | Rate (lb/A) | Green Foxtail | A | | B | | C | | D | | E | | AVG | |
|---|---|---|---|---|---|---|---|---|---|---|---|---|---|---|
| | | | 1 | 2 | 1 | 2 | 1 | 2 | 1 | 2 | 1 | 2 | 1 | 2 |
| COMMAND ® + 2 | 0.03125 + 0.125 | 25 | 0 | 0 | 0 | 0 | 0 | 0 | 0 | 0 | 0 | 0 | 0 | 0 |
| | 0.03125 + 0.25 | 10 | 0 | 0 | 0 | 0 | 0 | 0 | 0 | 0 | 0 | 0 | 0 | 0 |
| | 0.03125 + 0.50 | 35 | 0 | 0 | 0 | 0 | 0 | 0 | 0 | 0 | 0 | 0 | 0 | 0 |
| COMMAND ® + 3 | 0.03125 + 0.125 | 0 | 0 | 0 | 0 | 0 | 0 | 0 | 0 | 0 | 0 | 0 | 0 | 0 |
| | 0.03125 + 0.25 | 0 | 0 | 0 | 0 | 0 | 0 | 0 | 0 | 0 | 0 | 0 | 0 | 0 |
| | 0.03125 + 0.50 | 10 | 0 | 0 | 0 | 0 | 0 | 0 | 0 | 0 | 0 | 0 | 0 | 0 |
| Control | 0 + 0 | 0 | 0 | 0 | 0 | 0 | 0 | 0 | 0 | 0 | 0 | 0 | 0 | 0 |
| COMMAND ® | 0.0625 | 20 | 5 | 5 | 5 | 0 | 10 | 0 | 5 | 15 | 0 | 0 | 5 | 4 |
| COMMAND ® + 1 | 0.0625 + 0.25 | 15 | 5 | 0 | 5 | 20 | 0 | 15 | 5 | 0 | 5 | 15 | 4 | 10 |
| | 0.0625 + 0.50 | 0 | 0 | 0 | 0 | 0 | 0 | 0 | 0 | 0 | 0 | 0 | 0 | 0 |
| | 0.0625 + 1.0 | 20 | 20 | 15 | 5 | 0 | 20 | 0 | 20 | 0 | 5 | 0 | 14 | 3 |
| COMMAND ® + 2 | 0.0625 + 0.125 | 65 | 10 | 0 | 5 | 0 | 5 | 0 | 10 | 0 | 0 | 0 | 6 | 0 |
| | 0.0625 + 0.25 | 10 | 0 | 0 | 0 | 0 | 0 | 0 | 0 | 0 | 0 | 0 | 0 | 0 |
| | 0.0625 + 0.5 | 80 | 15 | 10 | 5 | 0 | 5 | 0 | 10 | 5 | 5 | 0 | 7 | 2 |
| COMMAND ® + 3 | 0.0625 0.125 | 30 | 5 | 0 | 5 | 0 | 3 | 0 | 10 | 5 | 5 | 0 | 6 | 1 |
| | 0.0625 0.25 | 35 | 3 | 0 | 0 | 0 | 0 | 0 | 5 | 0 | 0 | 0 | 2 | 0 |
| | 0.0625 0.50 | 35 | 10 | 5 | 0 | 0 | 0 | 0 | 10 | 0 | 0 | 0 | 4 | 1 |
| Control | 0 + 0 | 0 | 0 | 0 | 0 | 0 | 0 | 0 | 0 | 0 | 0 | 0 | 0 | 0 |
| COMMAND ® | 0.125 + 0 | 90 | 50 | 70 | 20 | 10 | 5 | 20 | 20 | 30 | 10 | 0 | 21 | 26 |
| COMMAND ® + 1 | 0.125 + 0.25 | 85 | 35 | 25 | 30 | 0 | 10 | 0 | 10 | 20 | 5 | 0 | 18 | 9 |
| | 0.125 + 0.50 | 60 | 15 | 5 | 10 | 0 | 5 | 0 | 20 | 0 | 20 | 0 | 14 | 1 |
| | 0.125 + 1.0 | 80 | 50 | 75 | 40 | 20 | 40 | 20 | 40 | 20 | 35 | 0 | 41 | 27 |
| COMMAND ® + 2 | 0.125 + 0.125 | 90 | 10 | 0 | 30 | 0 | 5 | 5 | 20 | 10 | 15 | 0 | 15 | 3 |
| | 0.125 + 0.25 | 50 | 10 | 0 | 15 | 5 | 10 | 0 | 30 | 15 | 15 | 0 | 16 | 4 |
| | 0.125 + 0.50 | 95 | 40 | 15 | 40 | 0 | 40 | 0 | 70 | 40 | 35 | 10 | 45 | 13 |
| COMMAND ® + 3 | 0.125 + 0.125 | 95 | 30 | 5 | 20 | 0 | 15 | 0 | 40 | 35 | 20 | 0 | 25 | 8 |
| | 0.125 + 0.25 | 100 | 15 | 15 | 10 | 10 | 15 | 5 | 25 | 0 | 15 | 0 | 15 | 4 |
| | 0.125 + 0.50 | 100 | 35 | 0 | 25 | 10 | 15 | 10 | 35 | 0 | 20 | 0 | 25 | 4 |
| Control | 0 + 0 | 0 | 0 | 0 | 0 | 0 | 0 | 0 | 0 | 0 | 0 | 0 | 0 | 0 |
| COMMAND ® | 0.25 + 0 | 100 | 75 | 50 | 70 | 40 | 65 | 35 | 50 | 50 | 50 | 35 | 62 | 42 |
| COMMAND ® + 1 | 0.25 + 0.25 | 100 | 100 | 100 | 75 | 50 | 70 | 40 | 75 | 75 | 50 | 0 | 74 | 53 |
| | 0.25 + 0.50 | 100 | 25 | 80 | 65 | 40 | 50 | 30 | 50 | 20 | 40 | 20 | 46 | 38 |
| | 0.25 + 1.0 | 100 | 100 | 100 | 85 | 75 | 65 | 40 | 65 | 40 | 65 | 35 | 76 | 58 |
| COMMAND ® + 2 | 0.25 + 0.125 | 100 | 100 | 100 | 75 | 45 | 70 | 30 | 75 | 50 | 40 | 5 | 72 | 46 |
| | 0.25 + 0.25 | 100 | 35 | 60 | 35 | 20 | 25 | 20 | 50 | 40 | 20 | 0 | 33 | 28 |
| | 0.25 + 0.50 | 100 | 75 | 75 | 75 | 50 | 50 | 50 | 75 | 40 | 70 | 45 | 69 | 52 |
| COMMAND ® + 3 | 0.25 + 0.125 | 100 | 100 | 100 | 75 | 35 | 75 | 50 | 75 | 75 | 35 | 50 | 72 | 62 |

TABLE II-continued

MEAN PERCENT CORN TOLERANCE AND WEED CONTROL 27 DAYS AFTER TREATMENT

| Herbicide & Antidote | Rate (lb/A) | Green Foxtail | \multicolumn{12}{c}{Corn Variety Tolerance} |
| | | | A | | B | | C | | D | | E | | AVG | |
| | | | 1 | 2 | 1 | 2 | 1 | 2 | 1 | 2 | 1 | 2 | 1 | 2 |
|---|---|---|---|---|---|---|---|---|---|---|---|---|---|---|
| | 0.25 + 0.25 | 90 | 35 | 35 | 35 | 35 | 30 | 25 | 35 | 30 | 35 | 30 | 34 | 31 |
| | 0.25 + 0.50 | 98 | 75 | 70 | 75 | 40 | 40 | 20 | 60 | 20 | 40 | 25 | 58 | 35 |
| Control | 0 + 0 | 0 | 0 | 0 | 0 | 0 | 0 | 0 | 0 | 0 | 0 | 0 | 0 | 0 |

1 = Pigment loss (incidence of bleaching and chlorosis)
2 = Stunting
A. COMMAND ® 2-(2-chlorophenyl)methyl-4, 4-dimethyl-3-isoxazolidinone

EXAMPLE 2

The experimental conditions were as described in Example 1. However, both COMMAND® and ERADICANE® were applied to sandy loam soil by pre-plant incorporation 3 inch deep. Seeds of giant foxtail and two corn hybrids were planted, 2 cm deep in aluminum flats.

An objective of this test was to determine if additional amounts of Compound 2 would be required to antidote COMMAND® injury. ERADICANE® contains a 24:1 ratio of ERADICANE® to Compound 2; additional mixtures were made to contain a 12:1 and 6:1 ratio of ERADICANE® to Compound 2. These mixtures were applied pre-plant incorporation to 1.0, 1.5, 2.0 and 3.0 oz/A COMMAND®. The results are exhibited in Table III.

TABLE III

ANTIDOTING OF COMMAND INJURY BY ERADICANE 11 DAYS AFTER TREATMENT

| Herbicide[1] Treatment | Rate (oz/A + lb/A) | % Corn Variety Tolerance[3] | | |
| | | GF[2] | A | B[4] |
|---|---|---|---|---|
| COMMAND ® | 1.0 + 0 | 82 | 37.0 | 30.0 |
| COMMAND ® + ERADICANE ® | 1.0 + 4.0 | 99 | 2.0 | 7.0 |
| COMMAND ® + ERADICANE ® 2X | 1.0 + 4.0 | 83 | 0.0 | 3.0 |
| COMMAND ® + ERADICANE ® 4X | 1.0 + 4.0 | 96 | 0.0 | 7.0 |
| COMMAND ® | 1.5 + 0 | 75 | 43.0 | 47.0 |
| COMMAND ® + ERADICANE ® | 1.5 + 4.0 | 98 | 7.0 | 17.0 |
| COMMAND ® + ERADICANE ® 2X | 1.5 + 4.0 | 88 | 8.0 | 10.0 |
| COMMAND ® + ERADICANE ® 4X | 1.5 + 4.0 | 98 | 5.0 | 12.0 |
| COMMAND ® | 2.0 + 0 | 92 | 63.0 | 60.0 |
| COMMAND ® + ERADICANE ® | 2.0 + 4.0 | 95 | 20.0 | 18.0 |
| COMMAND ® + ERADICANE ® 2X | 2.0 + 4.0 | 95 | 22.0 | 23.0 |
| COMMAND ® + ERADICANE ® 4X | 2.0 + 4.0 | 100 | 22.0 | 25.0 |
| COMMAND ® | 3.0 + 0 | 98 | 78.0 | 75.0 |
| COMMAND ® + ERADICANE ® | 3.0 + 4.0 | 95 | 60.0 | 63.0 |
| COMMAND ®+ ERADICANE ® 2X | 3.0 + 4.0 | 99 | 37.0 | 45.0 |
| COMMAND ® + ERADICANE ® 4X | 3.0 + 4.0 | 100 | 30.0 | 38.0 |

[1]COMMAND ® = 2 - (2-chlorophenyl)methyl-4,4 dimethyl-3-isoxazolidinone
ERADICANE ® = S-ethyl-N,N, dipropylthiocarbamate (EPTC) plus 2,2,5-trimethyl 3-(dichloroacetyl)-1,3-oxazolidine (Compound 2)
ERADICANE ® contains a 24:1 ratio of EPTC to Compound 2, ERADICANE ® 2x contains a 12:1 ratio of EPTC to Compound 2 ERADICANE ® 4X contains a 6:1 ratio of EPTC to Compound 2
[2]GF = Giant Foxtail at 28 DAT
[3]Mean % pigment loss
[4]A = CN 656
B = CN 8711

ERADICANE® reduced COMMAND® injury on both corn hybrids. Increasing the ratio of antidote compound No. 2 did not further reduce corn injury with rates of COMMAND® between 1–2 oz/A. When 3.0 oz/A COMMAND® was applied severe corn injury was observed. Additional antidote applied with ERADICANE® (2× and 4× treatments) antidoted COMMAND® injury significantly better than ERADICANE® alone.

EXAMPLE 3

Field experiments were conducted using a randomized block design with three replications per treatment. COMMAND® or COMMAND® and ERADICANE® 6.7-E formulated as an emulsifable concentrate were tank mixed and pre-plant incorporated into the soil. ERADICANE® 6.7-E was applied at the rate of 4 lb/A. COMMAND® was applied at the rate of 0.062, 0.125, 0.250 and 0.375 lb/A. Field corn, P3475, a moderately tolerant hybrid to COMMAND® injury and P3377, a susceptible hybrid to COMMAND® injury were seeded on the same day as treatment. Corn injury and weed control were evaluated 10 and 27 days after treatment (Tables IV and V) as hereinabove discussed.

The percent chlorosis exhibited in both corn hybrids at 10 and 27 days after treatment increased with increased application rates of COMMAND®. When ERADICANE® was applied the percent chlorosis of both corn hybrids significantly decreased at the higher rates of COMMAND® application.

TABLE IV

MEAN PERCENT CORN INJURY AND WEED CONTROL TEN DAYS AFTER TREATMENT

| Herbicide[1] Treatment | Rate (lb/A) | Giant Fox-tail | Velvet Leaf | Redroot Pigweed | Corn Variety Injury[2] A | B[3] |
|---|---|---|---|---|---|---|
| ERADICANE ® | 4.0 | 90 | 100 | 100 | 0 | 0 |
| ERADICANE ® + COMMAND ® | 4.0 + 0.062 | 98 | 100 | 100 | 13 | 10 |
| ERADICANE ® + COMMAND ® | 4.0 + 0.125 | 100 | 100 | 100 | 15 | 2 |
| ERADICANE ® + COMMAND ® | 4.0 + 0.25 | 100 | 100 | 100 | 63 | 30 |
| ERADICANE ®+ COMMAND ® | 4.0 + 0.375 | 100 | 100 | 100 | 73 | 37 |
| COMMAND ® | 0.062 | 22 | 55 | 42 | 18 | 8 |
| COMMAND ® | 0.125 | 38 | 32 | 52 | 63 | 23 |
| COMMAND ® | 0.25 | 65 | 93 | 77 | 78 | 63 |
| COMMAND ® | 0.375 | 88 | 97 | 97 | 90 | 78 |
| Control | | 0 | 0 | 0 | 2 | 0 |

[1]ERADICANE ® = EPTC (S-ethyl-dipropylthiocarbamate) plus antidote Compound No. 2 (2,2,5-trimethyl-3-(dichloroacetyl)-1, 3 oxazolidine)
COMMAND ® = 2-(2-chlorophenyl)methyl-4,4-dimethyl-3-isoxazolidinone
[2]% clorosis
[3]A = Zea mays P3377 (susceptible hybrid to COMMAND ® injury)
B = Zea mays P3475 (moderately tolerant hybrid to COMMAND ® injury)

TABLE V

MEAN PERCENT CORN INJURY AND WEED CONTROL 27 DAYS AFTER TREATMENT

| Herbicide[1] Treatment | Rate (lb/A) | Giant Fox-tail | Velvet Leaf | Redroot Pigweed | Corn Variety Injury[2] A | B[3] |
|---|---|---|---|---|---|---|
| ERADICANE ® | 4.0 | 100 | 100 | 100 | 0 | 0 |
| ERADICANE ® + COMMAND ® | 4.0 + 0.062 | 100 | 100 | 100 | 4 | 2 |
| ERADICANE ® + COMMAND ® | 4.0 + 0.125 | 100 | 100 | 100 | 17 | 3 |
| ERADICANE ® + COMMAND ® | 4.0 + 0.25 | 100 | 100 | 100 | 30 | 12 |
| ERADICANE ® + COMMAND ® | 4.0 + 0.375 | 100 | 100 | 100 | 40 | 30 |
| COMMAND ® | 0.062 | 13 | 82 | 98 | 3 | 1 |
| COMMAND ® | 0.125 | 67 | 100 | 100 | 21 | 11 |
| COMMAND ® | 0.25 | 67 | 100 | 100 | 38 | 27 |
| COMMAND ® | 0.375 | 97 | 100 | 100 | 78 | 66 |
| Control | | 0 | 0 | 0 | 2 | 0 |

[1]ERADICANE ® = EPTC (S-ethyl-dipropylthiocarbamate) plus antidote Compound No. 2 (2,2,5-trimethyl-3-(dichloroacetyl)-1,3 oxazolidine)
COMMAND ® = 2-(2-chlorophenyl)methyl-4,4-dimethyl-3-isoxazolidinone
[2]% clorosis
[3]A = Zea mays P3377 (susceptible hybrid to COMMAND ® injury)
B = Zea mays P3475 (moderately tolerant hybrid to COMMAND ® injury)

EXAMPLE 4

Field experiments were conducted using a randomized block design with three replications per treatment. COMMAND® as an emulsifiable concentrate was sprayed and incorporated to 3 inches in the soil with or without the oxazolidine antidote. Each field plot was 6.6 feet by 20 feet. Plots were planted to corn and wheat. Two days after planting the plots were irrigated with water due to dry conditions. Thereafter, no supplemental irrigation was necessary. The crops were rated for % phytotoxicity (as % bleaching) at 8, 14 and 21 days after treatment. The results are exhibited in Table VI.

Injury from the high rate of COMMAND® (0.25 lb/A) was decreased with the antidote. The low rate of COMMAND® (0.125 lb/A) did not cause significant phytotoxicity and the antidote did not significantly reduce the small % of phytotoxicity. Wheat was not antidoted against COMMAND® at the rates applied.

TABLE VI

MEAN PERCENT CROP INJURY[1]

| | | Corn DK656 | | | Corn - Pioneer 3165 | | | Wheat - Saluda | | |
|---|---|---|---|---|---|---|---|---|---|---|
| | | Days After Treatment | | | | | | | | |
| Treatment[2] | Rate (lb/A) | 8 | 14 | 21 | 8 | 14 | 21 | 8 | 14 | 21 |
| COMMAND ® | 0.125 | 8 | 4 | 3 | 7 | 7 | 3 | 17 | 12 | 5 |
| COMMAND ® + Antidote | 0.125 0.167 | 2 | 0 | 1 | 2 | 0 | 1 | 17 | 25 | 18 |
| COMMAND ® | 0.25 | 43 | 23 | 17 | 18 | 23 | 17 | 53 | 38 | 32 |
| COMMAND ® + Antidote | 0.25 0.167 | 10 | 3 | 7 | 2 | 3 | 7 | 57 | 53 | 47 |
| Antidote | 0.167 | 3 | 0 | 3 | 3 | 0 | 3 | 0 | 2 | 0 |
| Control | 0 | 0 | 0 | 2 | 0 | 0 | 2 | 0 | 0 | 0 |

[1]% Bleaching
[2]COMMAND ® is 2-(2-chlorophenyl)methyl-4,4-dimethyl-3-isoxazolidinone
Antidote is 2,2,5-trimethyl-3-(dichloroacetyl)-1,3-oxazolidine The antidote compounds and compositions of the present invention can be used in any convenient form. Thus the antidote compounds can be formulated into emulsifiable liquids, emulsifiable concentrates, liquids, wettable powders, powders, granules, microcapsules, or any other convenient form. In its preferred form, an herbicidal antidote compound in a non-phytotoxic quantity with respect to the crop is admixed with a selected herbicide and incorporated into the soil prior to or after planting the seed or applied pre-emergence. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not effect the herbicidal activity of the herbicides except to render the activity selective with respect to beneficial crops.

The amount of antidote compound present can range between about 0.01 to about 30 parts by weight of antidote compound described herein per each part by weight of herbicide. The exact amount of antidote compound will usually be determined on economic ratios for the most effective amount usable. It is understood that a non-phytotoxic quantity of antidote compound with respect to a particular crop will be employed in the herbicidal compositions described herein.

Formulations

The compounds and compositions can be formulated in the same manner in which herbicides are generally formulated. The object of the formulation is to apply the compounds and compositions to the locus where control is desired by conventional method. The locus may include soil, seeds, seedlings, crop, crop seeds and vegetation.

Useful formulations of the compounds of this invention can be prepared in conventional ways. They include dusts, granules, microcapsules, pellets, solutions, suspensions, emulsions, wettable powders, emulsifiable concentrates and the like. Many of these may be applied directly to the locus. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active herbicide and antidote ingredient(s) and optionally at least one of (a) about 0.1% to 20% surfactant(s) and (b) about 1% to 9.9% solid or liquid inert diluent(s). More specifically, they can contain these ingredients in the following approximate proportions.

TABLE VII

|  | Active Herb. & Ant. Ingredients | Weight Percent* | |
| --- | --- | --- | --- |
|  |  | Diluent (s) | Surfactant (s) |
| Wettable Powders | 20–90 | 0–74 | 1–10 |
| Oil Suspensions Emulsions, Solutions (Including Emulsifiable Concentrates) | 3–50 | 40–95 | 0–15 |
| Aqueous Suspension | 10–50 | 40–84 | 1–20 |
| Dusts | 1–25 | 70–99 | 1–20 |
| Granules and Pellets | 0.1–95 | 5–99.9 | 0–15 |
| Compositions | 90–99 | 0–10 | 0–2 |

*Active ingredient plus at least one of a Surfactant or a Diluent equals 100 weight percent.

Lower or higher levels of active ingredient can be present depending on the intended use and the physical properties of the compound. Higher ratios of surfactant to active ingredient are sometimes desirable, and are achieved by incorporation into the formulation or by tank mixing.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom sprayers, hand sprayers or airplanes.

Wettable powders are finely divided compositions comprising a particular carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculate sawdust, and granular carbon.

Microcapsules and other slow release formulations are advantageous as formulations to deliver and distribute the active ingredients. Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 95% of the weight of the entire capsule, and may contain an amount of solvent in addition to the active materials. Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention as well as materials in their naturally occurring form. Examples of such carriers are vermiculite, starch sintered clay granules, kaolin, attapulgite clay, sawdust and granular carbon. Useful encapsulating materials include natural and synthetic rubbers, cellulosic materials, styrenebutadiene copolymers, polyacrylonitriles, polyacrylates, polyesters, polyamides, polyureas, polyurethanes and starch xanthates.

Emulsifiable concentrates consist of an oil solution of the formulant plus and emulsifying agent. Prior to use, the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dust and granules, and surface active wetting, dispersing and emulsifying agents. Fertilizers, e.g., ammonium nitrate urea and superphosphate, may also be included. Aids to rooting and growth, e.g., compost, manure, humus and sand, may also be included.

Alternatively, the compounds and compositions of this invention can be applied to a crop by addition to irrigation water supplied to the field to be treated. This method of application permits the penetration of the compositions into the soil as the water is absorbed therein.

As another alternative, the formulation can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers or airplanes.

It is claimed:

1. An herbicidal composition comprising: a) an herbicidally effective amount of a 3-isoxazolidinone herbicide having the formula

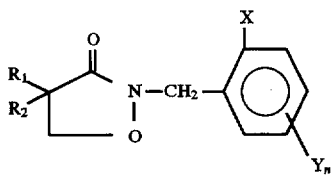

in which R1 and R2 are independently methyl or ethyl; X is hydrogen, methyl, chlorine, bromine or fluorine; Y is chlorine, bromine or fluorine, and n is 0, 1 or 2; b) a non-phytotoxic antidotally-effective amount, with respect to a corn crop, of an antidote compound of the formula

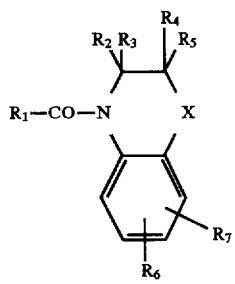

in which R1 is C1–C6 haloalkyl, R2–R5 are independently hydrogen or C1–C4 alkyl, R6 and R7 are hydrogen or halogen, and X is oxygen; and c) a herbicidally effective amount of one or more co-herbicides selected from acetamide herbicides, S-triazine herbicides, p-toluidine herbicides and sulfonylurea herbicides.

2. An herbicidal composition according to claim 1 wherein (c) is an S-triazine herbicide.

3. An herbicidal composition according to claim 1 wherein (c) is an acetamide herbicide.

4. An herbicidal compositions according to claim 3 wherein the acetamide herbicide is metolachlor.

5. An herbicidal composition according to claim 3 wherein the acetamide herbicide is alachlor.

6. An herbicidal composition according to claim 3 wherein the acetamide herbicide is acetochlor.

7. An herbicidal composition according to claim 1 wherein (c) is a sulfonylurea herbicide.

8. An herbicidal composition as defined in claim 1 wherein, said isoxazolidinone herbicide $R_1$ and $R_2$ are methyl.

9. An herbicidal composition as defined in claim 8 wherein said herbicidally active ingredient is 2-(2-chlorophenyl)methyl-4,4-dimethyl-3-isoxazolidinone.

10. An herbicidal composition as defined in claim 1 wherein said non-phytotoxic, antidotally effective antidote is 4-dichloroacetyl-3,4-dihydro-3-methyl-2H-1,4-benzoxazine.

11. An herbicidal composition as defined in claim 1 wherein the ratio of herbicide 3-isoxazolidinone to antidote ranges from between about 0.1:1 to about 30:1.

12. An herbicidal composition as defined in claim 11 wherein the ratio of herbicide 3-isoxazolidinone to antidote ranges from between about 1:1 to about 20:1.

13. A method of controlling undesirable vegetation in the presence of a corn crop comprising applying to the locus of said vegetation or said crop an herbicidally effective amount of a 3-isoxazolidinone herbicide having the formula

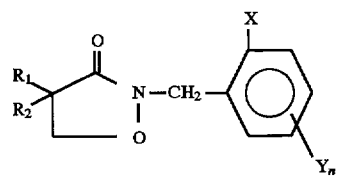

in which R1 and R2 are independently methyl or ethyl; X is hydrogen, methyl, chlorine, bromine or fluorine; Y is chlorine, bromine or fluorine, and n is 0, 1 or 2; b) a non-phytotoxic antidotally-effective amount, with respect to a corn crop, of an antidote compound of the formula

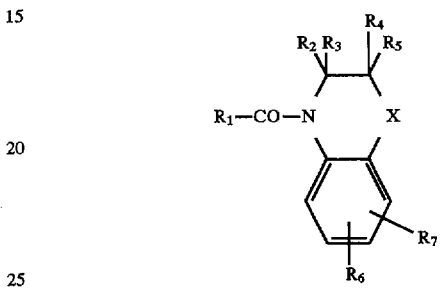

in which R1 is C1–C6 haloalkyl, R2–R5 are independently hydrogen or C1–C4 alkyl, R6 and R7 are hydrogen or halogen, and X is oxygen; and c) a herbicidally effective amount of one or more co-herbicides selected from acetamide herbicides, S-triazine herbicides, p-toluidine herbicides and sulfonylurea herbicides.

14. A method according to claim 13 wherein (c) is an S-triazine herbicide.

15. A method according to claim 13 wherein (c) is an acetamide herbicide.

16. A method according to claim 15 wherein the acetamide herbicide is metolachlor.

17. A method according to claim 15 wherein the acetamide herbicide is alachlor.

18. A method according to claim 15 wherein the acetamide herbicide is acetochlor.

19. A method according to claim 13 wherein (c) is a sulfonylurea herbicide.

20. A method according to claim 13 wherein the 3-isoxazolidinone herbicide and the herbicide of (c) are first combined into a composition and the composition is applied to the locus.

21. A method according to claim 20 in which the composition additionally includes the antidote.

22. A method according to claim 13 wherein said 3-isoxazolidinone herbicide is 2-(2-chlorophenyl)methyl-4,4-dimethyl-3-isoxazolidinone.

23. A method according to claim 13 wherein the ratio of 3-isoxazolidinone herbicide to antidote ranges from about 0.1:1 to about 30:1.

24. A method according to claim 13 wherein the 3-isoxazolidinone herbicide the antidote are first combined into a composition and the composition is applied to the locus.

25. A method according to claim 13 wherein the 3-isoxazolidinone herbicide is applied to the locus and the antidote is separately applied to the locus.

26. A method according to claim 13 wherein the antidote is applied as a seed treatment for the crop seed prior to planting.

27. A method according to claim 13 wherein said antidote compound is 4-dichloroacetyl-3,4-dihydro-3-methyl-2H-1,4-benzoxazine.

28. An herbicidal composition comprising: a) an herbicidally effective amount of a 3-isoxazolidinone herbicide having the formula

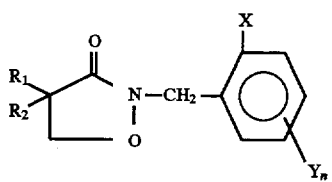

in which R1 and K2 are independently methyl or ethyl; X is hydrogen, methyl, chlorine, bromine or fluorine; Y is chlorine, bromine or fluorine, and n is 0, 1 or 2; b) a non-phytotoxic antidotally-effective amount, with respect to a corn crop, of an antidote compound of the formula

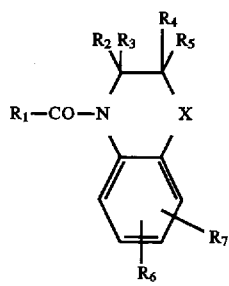

in which R1 is C1–C6 haloalkyl, R2–R5 are independently hydrogen or C1–C4 alkyl, R6 and R7 are hydrogen or halogen, and X is oxygen.

29. An herbicidal composition according to claim 28 further comprising one or more additional herbicidal compounds as co-herbicides.

30. An herbicidal composition as defined in claim 29 wherein said co-herbicide is a thiolcarbamate.

31. An herbicidal composition as defined in claim 30 wherein said thiolcarbamate is S-ethyl dipropylthiolcarbamate.

32. A composition according to claim 28 wherein said antidote compound is 4-dichloroacetyl-3,4-dihydro-3-methyl-2H-1,4-benzoxazine.

33. A method of controlling undesirable vegetation in the presence of a corn crop comprising applying to the locus of said vegetation or said crop an herbicidally effective amount of a 3-isoxazolidinone herbicide having the formula

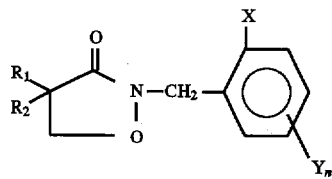

in which R1 and R2 are independently methyl or ethyl; X is hydrogen, methyl, chlorine, bromine or fluorine; Y is chlorine, bromine or fluorine, and n is 0, 1 or 2; b) a non-phytotoxic antidotally-effective amount, with respect to a corn crop, of an antidote compound of the formula

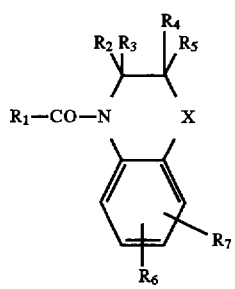

in which R1 is C1–C6 haloalkyl, R2–R5 are independently hydrogen or C1–C4 alkyl, R6 and R7 are hydrogen or halogen, and X is oxygen.

34. A method according to claim 33 further comprising one or more herbicidal compounds as co-herbicides.

35. A method according to claim 34 wherein said co-herbicide is a thiolcarbamate.

36. A method according to claim 35 wherein said thiolcarbamate is S-ethyl dipropyl thiolcarbamate.

37. A method according to claim 35 or 36 further comprising applying to said locus an amount of a thiolcarbamate extender effective to extend the soil life of the thiolcarbamate herbicide.

38. A method according to claim 37 wherein said antidote compound is 4-dichloroacetyl-3,4-dihydro-3-methyl-2H-1,4-benzoxazine.

* * * * *